US011857305B2

(12) United States Patent
Fhager et al.

(10) Patent No.: US 11,857,305 B2
(45) Date of Patent: Jan. 2, 2024

(54) SYSTEM AND METHOD FOR DETECTING AN ASSYMETRICALLY POSITIONED INTERNAL OBJECT IN A BODY

(71) Applicant: MEDFIELD DIAGNOSTICS AB, Gothenburg (SE)

(72) Inventors: Andreas Fhager, Vallda (SE); Mikael Persson, Alingsas (SE); Harald Jacobsson, Gothenburg (SE); Rikard Vinge, Gothenburg (SE)

(73) Assignee: MEDFIELD DIAGNOSTICS AB, Gothenburg (SE)

( * ) Notice: Subject to any disclaimer, the term of this patent is extended or adjusted under 35 U.S.C. 154(b) by 611 days.

(21) Appl. No.: 16/467,098

(22) PCT Filed: Dec. 5, 2017

(86) PCT No.: PCT/EP2017/081525
§ 371 (c)(1),
(2) Date: Jun. 6, 2019

(87) PCT Pub. No.: WO2018/104300
PCT Pub. Date: Jun. 14, 2018

(65) Prior Publication Data
US 2019/0313937 A1 Oct. 17, 2019

Related U.S. Application Data

(60) Provisional application No. 62/430,741, filed on Dec. 6, 2016, provisional application No. 62/430,754, filed on Dec. 6, 2016.

(51) Int. Cl.
*A61B 5/05* (2021.01)
*A61B 5/00* (2006.01)
*A61B 5/0507* (2021.01)

(52) U.S. Cl.
CPC .............. *A61B 5/0507* (2013.01); *A61B 5/72* (2013.01)

(58) Field of Classification Search
CPC ............ A61B 5/0507; A61B 5/72; A61B 5/05
See application file for complete search history.

(56) References Cited

U.S. PATENT DOCUMENTS 6,454,711 B1   9/2002  Haddad et al.
7,122,012 B2  10/2006  Bouton et al.
(Continued)

FOREIGN PATENT DOCUMENTS

CN       105120756 A   12/2015
EP         2020915      2/2009
(Continued)

OTHER PUBLICATIONS

Chandra, R., et al., "On the Opportunities and Challenges in Microwave Medical Sensing and Imaging," in IEEE Transactions on Biomedical Engineering, vol. 62, No. 7, pp. 1667-1682, Jul. 2015 (Year: 2015).*

(Continued)

*Primary Examiner* — Christopher Koharski
*Assistant Examiner* — Renee C Langhals
(74) *Attorney, Agent, or Firm* — NIXON & VANDERHYE

(57) ABSTRACT

Disclosed is a system for detecting an internal object in a body. The system includes at least one antenna pair including two antennas which are adapted to be symmetrically positioned around the body in relation to a line of symmetry. The system is adapted to transmit microwave signal into the body which are reflected and/or scattered from the internal object. The system is adapted to receive the reflected and/or scattered microwave signals, and to compare the received microwave signals at the symmetrically positioned antennas.

(Continued)

The system is adapted to detect the internal object or a change in an already detected internal object when there is a difference between the received microwave signals at symmetric antenna pairs. The difference is related to the different dielectric properties between the internal object and the body.

19 Claims, 7 Drawing Sheets

(56)  References Cited

U.S. PATENT DOCUMENTS

| | | | |
|---|---|---|---|
| 7,226,415 B2 | 6/2007 | Haddad et al. | |
| 8,724,864 B2* | 5/2014 | Persson | A61B 5/4312 382/128 |
| 9,072,449 B2 | 7/2015 | Semenov | |
| 9,414,749 B2 | 8/2016 | Semenov | |
| 2004/0077943 A1 | 4/2004 | Meaney et al. | |
| 2009/0015832 A1* | 1/2009 | Popovic | A61B 5/0507 356/342 |
| 2011/0267074 A1 | 11/2011 | Xie et al. | |
| 2014/0243647 A1* | 8/2014 | Clark | A61B 5/746 600/407 |
| 2015/0342472 A1 | 3/2015 | Semenov | |
| 2017/0143231 A1* | 5/2017 | Østberg | A61B 5/02042 |

FOREIGN PATENT DOCUMENTS

| | | |
|---|---|---|
| EP | 2032030 | 3/2009 |
| EP | 2457195 | 5/2012 |
| WO | WO2007/136334 | 11/2007 |
| WO | WO2008/002251 | 1/2008 |
| WO | WO2011/009945 | 1/2011 |
| WO | WO2011/135413 | 11/2011 |
| WO | 2013/110001 | 7/2013 |
| WO | WO2014/141268 | 9/2014 |

OTHER PUBLICATIONS

Rezaeieh, S. A., Zamani, A., Bialkowski, K. S., Mahmoud, A., & Abbosh, A. M. (2015). Feasibility of using wideband microwave system for non-invasive detection and monitoring of pulmonary oedema. Scientific reports, 5(1), 14047. (Year: 2015).*
Office Action issued in Chinese Patent Application No. 201780083488.0 dated Oct. 8, 2022.
International Search Report—PCT/EP2017/081525—dated Feb. 7, 2019.

* cited by examiner

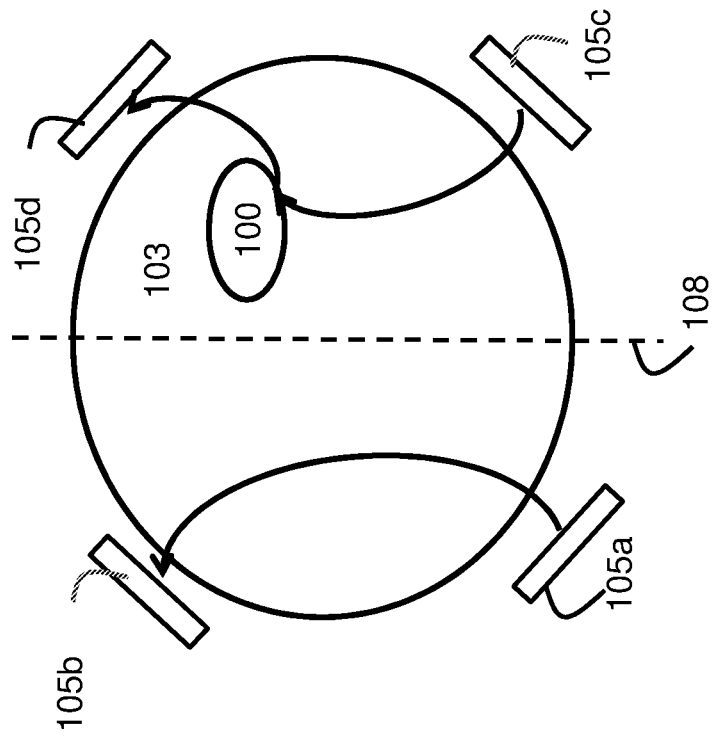
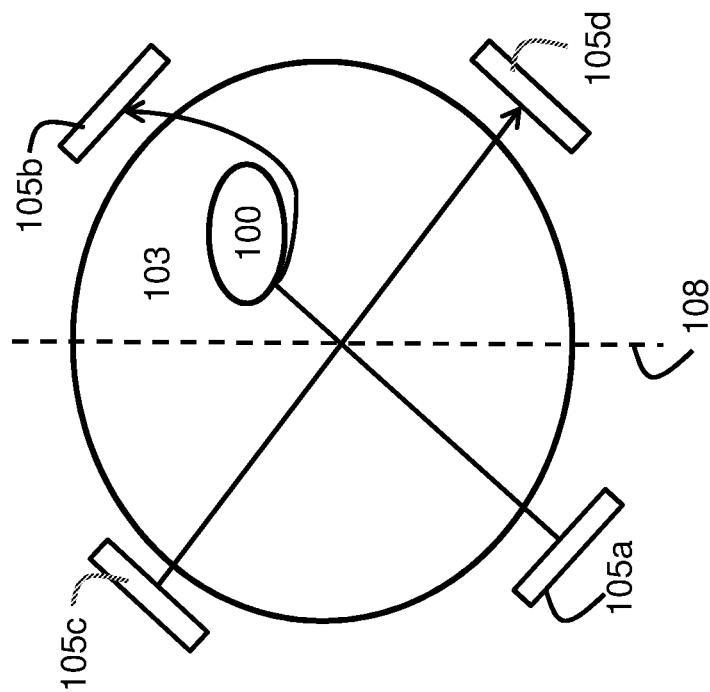

SYSTEM AND METHOD FOR DETECTING AN ASSYMETRICALLY POSITIONED INTERNAL OBJECT IN A BODY

TECHNICAL FIELD

Embodiments herein relate generally to a system and a method. More particularly the embodiments herein relate to detecting an asymmetrically positioned internal object in a body.

BACKGROUND

Non-invasive techniques for diagnosis and determination of status of humans or animals are increasingly winning ground since these poses low risk for the patient and are usually low cost as compared to invasive techniques. Especially considering the brain, non-invasive techniques may provide convenient and safe ways of determination of the brain status. However, the common techniques for this are not able to determine all types of parameters of need, which means that there are blind spots where invasive techniques are still used.

Furthermore, some non-invasive techniques provide solutions where the patient is still put in risk of danger, for instance where x-rays are used the patient will be subjected to a dose of radiation potentially harmful and it can in many cases not be used for continuously or semi-continuously, i.e. intermittently, monitor the status of parameters in the brain or in any other part of the body.

The use of conventional non-invasive techniques for pre-hospital applications is limited, for example Computed Tomography (CT) and Magnetic Resonance Imaging (MRI) systems are too large and costly for ambulance use. Other already portable systems, such as ultrasound systems, are not always suitable for the particular diagnostic need. New portable systems for pre-hospital use are therefore needed.

Detection of haemorrhages in the brain caused by any form of head trauma, or detection of haemorrhages in any other part of the body could be made with the same underlying technology. In the head, intracranial bleedings constitute a risk of developing lethal intracranial pressure. In severe cases, such as traffic accidents, patients might develop lethal intracranial pressure within one or two hours. These patients can often be treated successfully with surgical or other interventions in the treatment is started early after the injury. It requires transportation to the right hospital where such neuro-surgery expertise is available. A person with an intracranial bleeding might initially look healthy seem unaffected and there is a significant risk that these patients get transported to a closer hospital without neuro-surgery expertise. This will likely be lethal for the patients. If the presence of an intracranial bleeding is detected too late the patient might be dead before arriving at a hospital where neuro-surgery interventions could have saved the life of the patient. The underlying challenge here is that no system exists at present that with sufficient accuracy can diagnose or predict which patents have suffered head trauma that have led to an intracranial bleeding.

The standard method to detect intracranial bleedings is by CT or MRI, but this has to be done at hospitals and thus valuable time is lost before treatment can be started. Other experimental techniques for pre-hospital diagnostics exist and are under clinical evaluation, but no systems showing adequate sensitivity and specificity of haemorrhages have yet reached the market.

Delays in diagnosing stroke patients is today a major problem as many patients do not get a diagnosis in time, and therefore treatment are often significantly delayed with dramatic consequences for the patients. Delays in the treatment increase the risk of severe injuries, handicaps, and even death.

Ambulance service paramedics are trained to use a stroke recognition tool to speed up transfer and assessment of patients with suspected stroke. This facilitates the time critical intervention of thrombolysis which has been shown to improve the outcome from ischemic stroke if given in time. Even with the best efforts today, many patients still don't get the treatment in time. It is also difficult to distinguish between healthy people and stroke patients, and further to diagnose between ischemic and hemorrhagic stroke. With portable systems that could diagnose between ischemic and hemorrhagic strokes in a pre-hospital setting many patients could get better treatment and thereby the patient outcome could be better. As an example, the possibility to diagnose patients with ischemic stroke from patients with hemorrhagic stroke would enable to better optimize the initial management of the patients. It would also be possible to consider giving clot resolving medicine patients with ischemic stroke before reaching the hospital.

Other example where today's technology does not provide any solution is for long term monitoring of patients with an increased risk of getting a stroke. Monitoring of high risk patients during sleep or while the patient lies down in bed would be a helpful tool in early detection of a potential stroke. In patients that have had an intracranial bleeding monitoring is a way to detect if the bleeding starts over. There exist also a number of other monitoring situations where it is of interest to monitor the occurrence, presence, or changes in a present bleeding, or other types of liquids, e.g. edemas. Applications, such as bedside monitoring of intracranial pressure would also be desired in many clinical situations. Neither CT, MRI nor ultrasound are suitable or practical for these type of monitoring applications. CT is also unsafe as it would expose the patients for long periods of x-ray exposure.

Apart from the above-mentioned limitations in today's technology for detecting internal properties related to medical conditions in patients, there are several applications in industry where today's technology has significant limitations to detect internal properties or changes of different internal bodies.

To exemplify, there has been an increased demand from wood processing industry for non-destructive techniques to detect and quantify internal defects and variations in trees and wood products. Sensor systems are of interest to the wood and timber industry where different choices in the phases of thinning, logging and at the sawmill affect the net production and thus the revenue of the industry. For example, information about the interior of the wood could be used for optimizing the different phases of the production chain and with automatized and easy to use systems the optimization could be made down to individual logs. In the forest, it could be advantageous to determine the quality of the trees before thinning, or logging. Trees could for example be affected by tree rot which cannot be seen from the outside but seriously degrades the quality of the tree. Such trees should ideally be removed already when thinning the forest. The possibility of identifying internal defects, such as knots and nails, can help optimize the production and to avoid costly damage to the saw blade and other tools.

EP2020915B1 describes a method and a system to reconstruct images from microwave measurement data.

EP2032030B1 describes a device, method, and system for monitoring the status of an internal part of a body using an electromagnetic transceiver operating in the microwave regime; microwave measurement data in from of time domain pulses are analysed to determine the location of the surface of the body (e.g. skin) and thereby enable compensation for movements.

EP2457195 B1 describes a device for determining an internal condition of a subject by analysis of an enclosed volume, by using a particular statistical classification algorithm, using training data.

U.S. Pat. No. 7,226,415 B2 describes an apparatus for detecting blood flow based on the differences in dielectric properties of tissue.

U.S. Pat. No. 6,454,711 B1 relates to a haemorrhage detector. It describes an antenna array including matching medium between antennas and the skin, as well as damping material between antennas. The detection algorithm is based on analysing time domain pulses and their changes du to haemorrhages.

U.S. Pat. No. 7,122,012 B2 describes a method of detecting a change in the level of fluid in tissue. The analysis is based on comparing the measurements with reference measurements on a target without the liquid present. The presence of fluid is based on differences between a base line signal and a measured signal.

U.S. Pat. No. 9,072,449 B2 disclose a system for wearable/man-portable electromagnetic tomographic imaging includes a wearable/man-portable boundary apparatus adapted to receive a biological object within, a position determination system, electromagnetic transmitting/receiving hardware, and a hub computer system.

U.S. Pat. No. 9,414,749 B2 discloses an electromagnetic tomography system for gathering measurement data pertaining to a human head includes an image chamber unit, a control system, and a housing. The image chamber unit includes an antenna assembly defining a horizontally-oriented imaging chamber and including an array of antennas arranged around the imaging chamber. The antennas include at least some transmitting antennas and some receiving antennas. The control system causes the transmitting antennas to transmit a low power electromagnetic field that is received by the receiving antennas after passing through a patient's head in the imaging chamber. A data tensor is produced that may be inversed to reconstruct a 3D distribution of dielectric properties within the head and to create an image. The housing at least partially contains the antenna assembly and has a front entry opening into the imaging chamber. The head is inserted horizontally through the front entry opening and into the imaging chamber.

US20150342472A1 discloses a method of assessing status of a biological tissue includes irradiating an electromagnetic signal, via a probe, into a biological tissue. The irradiated electromagnetic signal is received after being scattered/reflected by the biological tissue. Blood flow information pertaining to the biological tissue is provided, and the received signal is analyzed based at least upon the provided blood flow information and upon knowledge of electromagnetic signal differences in normal, suspicious, and abnormal tissue. Using a dielectric properties reconstruction algorithm, dielectric properties of the biological tissue are reconstructed based at least upon results of the analyzing step and upon blood flow information, and using a tissue properties reconstruction algorithm, tissue properties of the biological tissue are reconstructed based at least in part upon results of the reconstructing step and upon blood flow information.

Therefore, there is a need to at least mitigate or solve the above issues.

SUMMARY

An objective of embodiments herein is therefore to obviate at least one of the above disadvantages and to provide improved detection of an internal object in a body.

According to a first aspect, the object is achieved by a system for detecting an internal object in a body. The internal object and the body have different dielectric properties. The system comprises at least one antenna pair comprising two antennas which are adapted to be symmetrically positioned around the body in relation to a line of symmetry in the body. The system is adapted to transmit one microwave signal or multiple microwave signals into the body from at least one of the antennas in the system. The transmitted microwave signals are reflected and/or scattered from the internal object. The system is adapted to receive the reflected and/or scattered microwave signals at the other antenna and/or at the transmitting antenna whereby it is operated as a receiver after it has transmitted or it is operated as a receiver at the same time as it is transmitting. The system is further adapted to compare the received microwave signals at the symmetrically positioned antennas, and to detect the internal object or a change in an already detected internal object when there is a difference between the received microwave signals at symmetric antenna pairs. The difference is related to the different dielectric properties between the internal object and the body.

According to a second aspect, the object is achieved by a method performed by a system for detecting an internal object in a body. The internal object and the body have different dielectric properties. The system comprises at least one antenna pair comprising two antennas which are adapted to be symmetrically positioned around the body in relation to a line of symmetry in the body. The system transmits one microwave signal or multiple microwave signals into the body from at least one of the antennas. The transmitted microwave signals are reflected and/or scattered from the internal object. The system receives the reflected and/or scattered microwave signals at the other antenna(s) and/or at the transmitting antenna whereby it is operated as a receiver after it has transmitted or it is operated as a receiver at the same time as it is transmitting. The system compares the received microwave signals at the symmetrically positioned antennas. The system detects the internal object or a change in an already detected internal object when there is a difference between the received microwave signals at symmetric antenna pairs. The difference is related to the different dielectric properties between the internal object and the body.

According to a third aspect, the object is achieved by an antenna system comprising at least one antenna pair comprising two antennas which are adapted to be symmetrically positioned around the body in relation to a line of symmetry in the body. The antenna system is adapted to transmit microwave signals into a body from at least one of the antennas. The transmitted microwave signals are reflected and/or scattered from an internal object in the body. The antenna system is adapted to receive the reflected and/or scattered microwave signals at the other antenna and/or at the transmitting antenna whereby it is operated as a receiver after it has transmitted or it is operated as a receiver at the same time as it is transmitting, or it can also be adapted to receive at the same time as it is transmitting. The antenna system is adapted to provide information associated with the received microwave signals to an analyzing unit.

The intended operation of the system is to detect an internal object or several internal objects that are located asymmetrically with respect to the symmetry line. Another intended operation is to detect the internal object by means of analyzing changes over time of the received microwave signals. Yet another intended operation is to detect changes of properties, such as increase of size, position, shape, dielectric properties, etc., in an already detected internal object by analyzing the differences between microwave signals received at different times. Changes in the received microwaves signals at different points in time are indicative of a change in properties of the internal object. The detection of internal objects is based on analyzing asymmetries and/or changes in the asymmetries in the received microwave signals. In other words, asymmetries in the received microwave signals make it possible to detect the internal object or the change in an already detected internal object. Improved detection of an internal object in a body is thus provided over analysing each signal separately.

Embodiments herein afford many advantages, of which a non-exhaustive list of examples follows:

While typically not used in the field of diagnostics, microwave signals are useful for various applications which require diagnosis. Microwave signals provide a non-invasive measurement deep into different types of bodies. Such measurements may provide useful information that is otherwise invisible to the human eye. Such non-invasive techniques for diagnosis and determination of status of bodies pose low risk for the object, e.g. a patient, and are involved with a low cost as compared to invasive techniques On advantage of the embodiments herein is that techniques based on microwave signals provide non-invasive, easy access, to bodies such as e.g. a human brain at a relatively low cost providing a large amount of multi frequency scattering data that can be used to analyze the continued developments of the dielectric and geometric properties of the body.

A further advantage is that a system based on microwave technology relatively easily can be built portable and lightweight. This makes the microwave technique particularly useful for pre-hospital diagnosis in for example ambulances or at an accident scene. Microwave technology is also suitable for the development of hand held units for field use, for example in the forest.

A further advantage of the embodiments herein is that in principle, all conditions inside a body where there is a dielectric contrast with respect to the surrounding dielectric properties and/or where the level of dielectric contrast changes over time may be detected.

Another advantage of the embodiments herein is that they provide solutions for handling microwave scattering data and provides a more reliable result for interpretation of the data and a more reliable diagnosis of the internal properties, i.e. the internal object, of the body under investigation.

The embodiments herein are not limited to the features and advantages mentioned above. A person skilled in the art will recognize additional features and advantages upon reading the following detailed description.

BRIEF DESCRIPTION OF THE DRAWINGS

The embodiments herein will now be further described in more detail in the following detailed description by reference to the appended drawings illustrating the embodiments and in which:

FIG. 1b is a schematic diagram illustrating an example of a system with two antenna pairs.

FIG. 1c is a schematic diagram illustrating an example of a system with two antenna pairs.

The drawings are not necessarily to scale and the dimensions of certain features may have been exaggerated for the sake of clarity. Emphasis is instead placed upon illustrating the principle of the embodiments herein.

DETAILED DESCRIPTION

The embodiments herein relate to detection of an internal object in a body, and more specifically an internal object that is asymmetrically positioned with respect to a symmetry line of the body. This may also be referred to as detection of one or more dielectric target, with certain properties, such as size, shape, position, dielectric parameters, etc. that is immersed inside another dielectric medium. A further description of the embodiments herein is that they relate to interrogating the interior of a larger object/body and to detect the presence, occurrence of variations in the properties of one or more immersed objects with different dielectric property than that of the larger object in the presence of microwave signals. The dielectric constant is the ratio of the permittivity of a substance to the permittivity of free space. The dielectric property of a substance is usually also referring to both the permittivity and conductivity of a substance and thereby the dielectric constant is represented in form of a complex number. The definition and implication of dielectric properties, represented as a permittivity, conductivity or a complex dielectric parameter is well known by a person skilled in the art of microwave theory and practice.

Figure 1A:
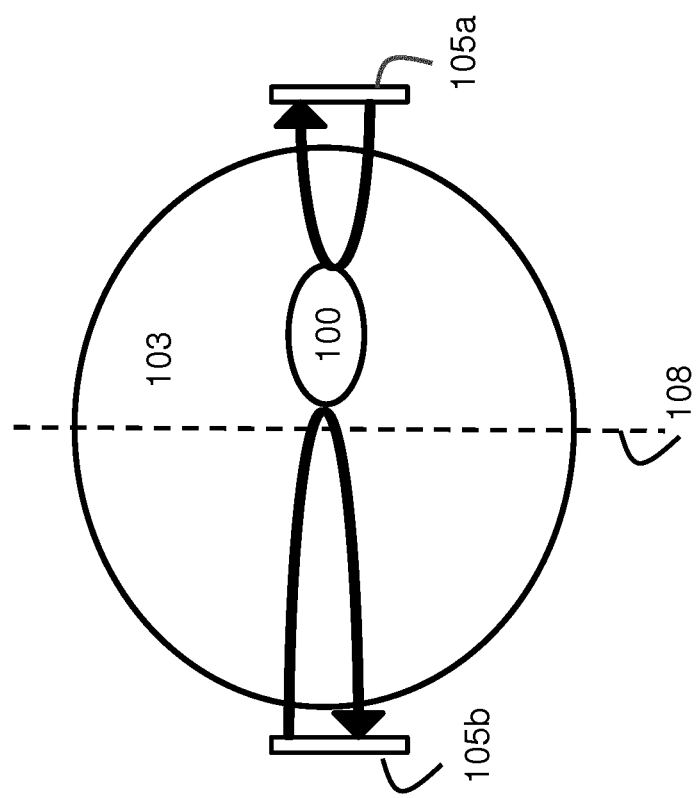
FIG. 1a is a schematic diagram illustrating an example of a system with one antenna pair.

FIG. 1a illustrates an example of a system for detecting an internal object 100 in a body 103. The internal object 100 and the body 103 are not parts of the system. The body 103 may be a head, a brain, an abdomen, a thorax, a leg or any other body part of a human, an animal, or it may be any other form of biological tissue such as for example a tree or wood. The body 103 may also be non-living tissue, and of non-biological origin, such as but not limited to plastics, etc. The body 103 may also be referred to as a dielectric medium, an object under investigation, a larger object, etc. The internal object 100 may also be referred to as an immersed object, a dielectric target, etc. The internal object 100 may be in the form of solid, semisolid, liquid or gas. The internal object 100 may be referred to as an immersed object in a larger object or body 103. The internal object 100 may also be referred to as a dielectric target, with certain properties, such as size, shape, position, dielectric parameters, etc. that is immersed inside another dielectric medium, i.e. the body 103. The internal object 100 may be a bleeding, a clot, an oedema, a nail, a twig etc. Note that FIG. 1a only illustrate one internal object 100, but any other number of internal objects 100 may be present in the body 103. One internal object 100 is shown for the sake of simplicity.

FIG. 1a further illustrates that an example where the system comprises two antennas 105 which are adapted to be symmetrically positioned around the body 103. The reference numbers for the antennas 105 in FIG. 1a are shown with the letters a and b, and this difference will be explained later. These two antennas 105 may be described as an antenna pair. Note that any other 2*n number of antennas 105 and n antenna pairs are applicable, where n is a positive integer. In the case one at least one antenna 105 or an odd integer number of antennas 105 are positioned at the symmetry line 108 the number of antennas could be 2n+1. One antenna in the pair may be a transmitter which is adapted to transmit microwave signals to be received by the other antenna which acts as a receiver. One antenna 105 in the pair may be a combined transmitter and receiver antenna, and the other antenna 105 may also be a combined transmitter and receiver antenna, i.e. both antennas 105 in the pair may act as both transmitter and receiver. In one such combined example of the system, both antennas 105 may be adapted to transmit and receive microwave signals from each other. In another such combined example of the system, each antenna 105 may be adapted to transmit and receive microwave signal from itself, i.e. the microwave signal is transmitted from one antenna 105, reflected by e.g. the internal object 100 or any other part of the body 103, and received at the same antenna 105.

The antennas 105 may be adapted to generate, transmit and receive electromagnetic signals in the microwave range. Microwave signals may be described as electromagnetic waves which have wavelengths in the range from one meter to one millimetre, and they have frequencies between 300 MHz (101 cm) and 300 GHz (0.1 cm). The term microwave is used herein when referring to electromagnetic signals in the microwave range.

The terms transmitter and transmitter antenna are used interchangeably herein. Similarly, the terms receiver and receiver antenna are used interchangeably herein.

The antennas 105 may of various types such as e.g. monopoles, patches, horns, etc. or any other suitable antenna type. Other types of emitters and or receivers can be used. The two antennas 105 in one pair is of the same type, and antennas 105 in two pairs can be of different types as long as they are of the same types within each pair.

Figure 1D:
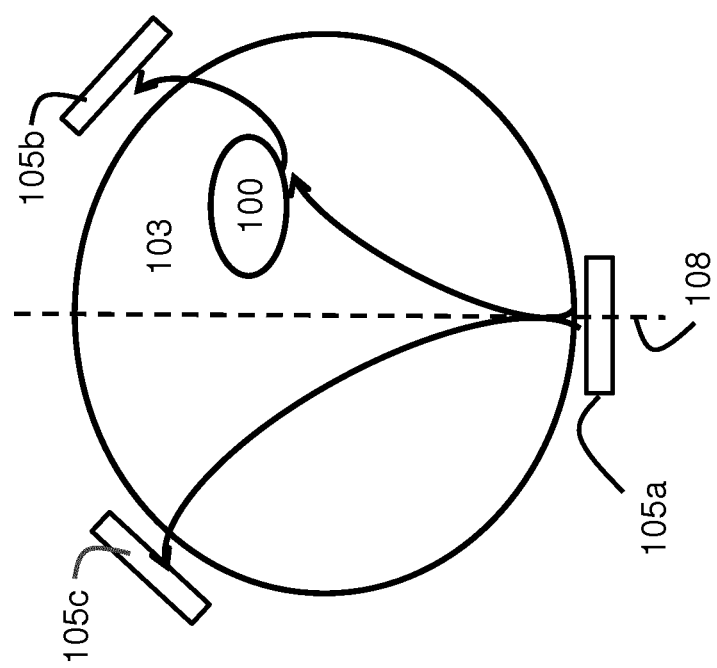
FIG. 1d is a schematic diagram illustrating an example of a system with two antenna pairs and where one antenna is common among the two pairs. This is a system with three antennas.

In one embodiment, the system may comprise a configuration of at least two antennas 105, where each antenna 105 acts both as transmitter and receiver, as illustrated in FIG. 1a. In another embodiment, it may comprise at least one separate transmitter antenna 105 and at least two separate receiver antennas 105 adapted to be positioned around the body 103 at positions that are symmetrically located with respect to the symmetry line 108, as illustrated in FIG. 1d. In yet another embodiment, the system may comprise at least four antennas 105 acting both as transmitters and receivers and positioned symmetrically around the body 103 at position that are symmetrically located with respect to the symmetry line 108, as illustrated in FIGS. 1b and 1c. A possible operation is that all antennas 105 in turn, are used as transmitters while the rest of the antennas 105 are receiving or alternatively a subset of antennas 105 in turn can be used simultaneously as transmitters while a subset of antennas 105 are receiving or alternatively all antennas 105 can be used as transmitters simultaneously and all the antennas 105 can be used as receivers simultaneously.

A measurement, when all combinations or a subset of antennas 105 are used as transmitter-receiver pairs are denoted a "full measurement set" in the following text. A measurement refers to the reflected and/or scattered microwave signal which is received by the receiving antenna 105. To obtain time resolution data, several "full measurement sets" after each other are collected during a period of time. Or alternatively, several partial measurement sets are measured, meaning that only a subset of all antennas 105 are used as transmitters and/or receivers. A different way to describe a "full measurement set" is that it constitutes the measurement of a given set of antenna combinations among the possible combinations of pairs out of all antennas 105. The meaning of time resolution data is thus that the same antenna combinations are measured repeatedly at two or more occasions in time. A "full measurement set" must be completely measured before a new "full measurement set" can be measured at a later time.

The body 103 may be substantially symmetric. The body 103 may have a symmetry line 108 which represents a division of the body 103 in two counterparts. The symmetry line 108 may also be referred to as a line of symmetry, a center line etc. For example, when the body 103 represents a human brain, the one side of the symmetry line 108 is the left side of the brain and the other side of the symmetry line 108 is the right side of the brain. Each body part on the side of the symmetry line 108 is substantially symmetric in both shape and in content.

In the example in FIG. 1a with two antennas 105, one antenna 105 is adapted to be positioned at a first position on the left side of the symmetry line 108 and the other antenna 105 adapted to be positioned at a second position on the right side of the symmetry line 108. Thus, the antennas 105 are adapted to be positioned at opposite positions around the body 103 with respect to the symmetry line 108. This may also be described as the antennas 105 are adapted to be symmetrically positioned around the body 103 in relation to a line of symmetry 108 in the body 103. The antennas 105 are divided into one or more subsets or pairs, that are adapted to be positioned around the body 103, and the antennas 105 are to be placed symmetrically in relation to a line of symmetry 108 in the body 103.

The system may further comprise a structure or arrangement (not illustrated in FIG. 1a) to which the antenna 105 are attached and which makes the system suitable to be positioned around the body 103. For example, the system may be a wearable system adapted to be worn by a person, in particular on the persons head. In such example the structure may have a head shape such as e.g. a helmet to which the antennas 105 may be attached. The antennas 105 may be fixed or releasable attached to such structure.

In a case where the internal object 100 is present in the body 103, it is assumed that the internal object 100 is located substantially on one side of the symmetry line 108. Thus, the internal object 100 may be on one of the body halves separated by the symmetry line 108. Or alternatively the internal object 100 can be located such that it is partly located on both sides of the symmetry line 108, but then the internal object 100 itself must be asymmetric with respect to the symmetry line 108, for example such that a larger part of the internal object 100 is located on one side of the symmetry line 108 and a smaller part on the other side. One of the antennas 105 may transmit a microwave signal in the direction towards the other antenna 105. Since the internal object 100 is located in the path of the microwave signal on its way from one antenna 105 to the other, the microwave signal propagates through the internal object 100 and it may also be scattered or reflected by the internal object 100. Consequently, the properties of the microwave signals when received at two receiver antennas 105 that are symmetrically positioned with respect to the symmetry line 108 are not the same as the properties of the received microwave signals at the same antennas 105 when the internal object 100 is not present. For example, the signal strength of the microwave signal may be different, the amount of signal may be different, the phase may be different etc. This difference will be described in more detail later.

On example of how the system with one antenna pair illustrated in FIG. 1a functions will now be shortly described. As mentioned earlier, the reference numbers for the antennas 105 in FIG. 1a have the letters a and b. These letters will be used when explaining the system. In this example, the first antenna 105a is a combined transmitter and receiver antenna and the second antenna 105b is also a combined transmitter and receiver antenna. The transmitter and receiver functions of each antenna 105 may always be enabled, or the antenna 105 may switch between enabling the transmitter and receiver function. The internal object 100 in the example of FIG. 1a is shown to be between the first antenna 105a and the second antenna 105b.

1) The first antenna 105a acts as a transmitter and transmits microwave signal into the internal object 100.
2) The microwave signal propagates into the body 103 and is reflected by the internal object 100.
3) The first antenna 105a acts as a receiver and receives the reflected microwave signal.
4) The second antenna 105b acts as a transmitter and transmits microwave signal into the internal object 100.
5) The microwave signal propagates into the body 103 and is reflected by the internal object 100.
6) The second antenna 105b acts as a receiver and receives the reflected microwave signal.
7) The two received reflected signals at the first antenna 105a and at the second antenna 105b are compared in order to detect any differences between them.

FIG. 1b illustrates an example of the system comprising four antennas 105, i.e. two antenna pairs. The system comprises a first antenna pair comprising a first antenna 105a and a second antenna 105b, and a second antenna pair comprising a third antenna 105c and a fourth antenna 105d. The first antenna 105a in the first pair is adapted to be a transmitter and the second antenna 105b in the first pair is adapted to be a receiver. The third antenna 105c in the second pair is adapted to be a transmitter and the fourth antenna 105d in the second pair is adapted to be a receiver. The transmitter and receiver within the antenna pair can be interchanged, so that the receiving antennas are operated as transmitters and then the transmitting antennas are operated as receivers. The internal object 100 is between the antennas in the first antenna pair. There is no internal object 100 between the antennas 105 in the second antenna pair.

1) The first antenna 105a in the first pair acts as a transmitter and transmits microwave signal towards the second antenna 105b, i.e. towards the other antenna in the first pair.
2) Microwave signal propagates through and is scattered and/or reflected by the internal object 100.
3) The second antenna 105b in the first par acts as a receiver and receives scattered microwave signal.
4) The third antenna 105c in the second pair acts as a transmitter and transmits microwave signal towards the fourth antenna 105d in the same pair.
5) Microwave signal propagates through body 103 because there is no internal object 100 in the signal path between these antennas.
6) The third antenna 105c in the second pair acts as a receiver and receives microwave signal from the fourth antenna 105d.
7) Compare microwave signals received at the fourth antenna 105d in the second pair and the second antenna 105b in the first pair.

In one of the antenna pairs, i.e. the pair where the path for the microwave signal is not interfered by the internal object 100, microwave signals with certain properties are received. In the other antenna pair, i.e. the pair where the path for the microwave signal is interfered by the internal object 100, microwave signals with different properties are received. For references, if the internal object 100 is not present the received signals in both antenna pairs are substantially identical as the measurement scenario for both antenna pairs are identical. When the internal object 100 is present the difference in the received microwave signals between the two antenna pairs are used as a means for detecting the internal object 100. This situation is referred to as that the measured signals are asymmetric. The microwave signals between at least two antenna pairs may be compared, i.e. resulting in symmetric signals, when no internal object 100 is present, or in asymmetric signals when the internal object 100 is present.

FIG. 1c illustrates a different configuration of the two antenna pairs that be used to analyze the presence of the internal object 100 in an analogous way as in FIG. 1b. In this case the first antenna 105a is adapted to be a transmitter and the second antenna 105b is adapted to be a receiver. The third antenna 105c is adapted to be a transmitter and the fourth antenna 105d is adapted to be a receiver. The transmitter and receiver within the antenna pair can be interchanged, so that the receiving antennas 105 are operated as transmitters and then the transmitting antennas 105 are operated as receivers.

FIG. 1d illustrates a case where one can imagine that the two transmitting antennas in the two pairs are collocated on a position on the symmetry line. In practice, the two antennas 105 are replaced with one single antenna 105. In that way two antenna pairs can be formed as illustrated in FIG. 1d. In this case the first antenna 105a is adapted to be a transmitter and the antennas 105b and 105c are adapted to be receivers. In this case antenna 105a is positioned on the symmetry line 108 and the antennas 105b and 105c are symmetrically positioned with respect to the symmetry line 108. It the internal object 100 is not present, antenna 105b and 105c receives identical microwave signals if antenna 105a transmits. If the internal object 100 is present the difference in the received microwave signals between the two antenna pairs are used as a means for detecting the internal object 100. The transmitter and receiver within the antenna pair can be interchanged, so that the receiving antennas 105 are operated as transmitters and then the transmitting antennas 105 are operated as receivers.

When the term "received microwave signals" refers to reflected or scattered electromagnetic waves in the microwave region.

Figure 2:
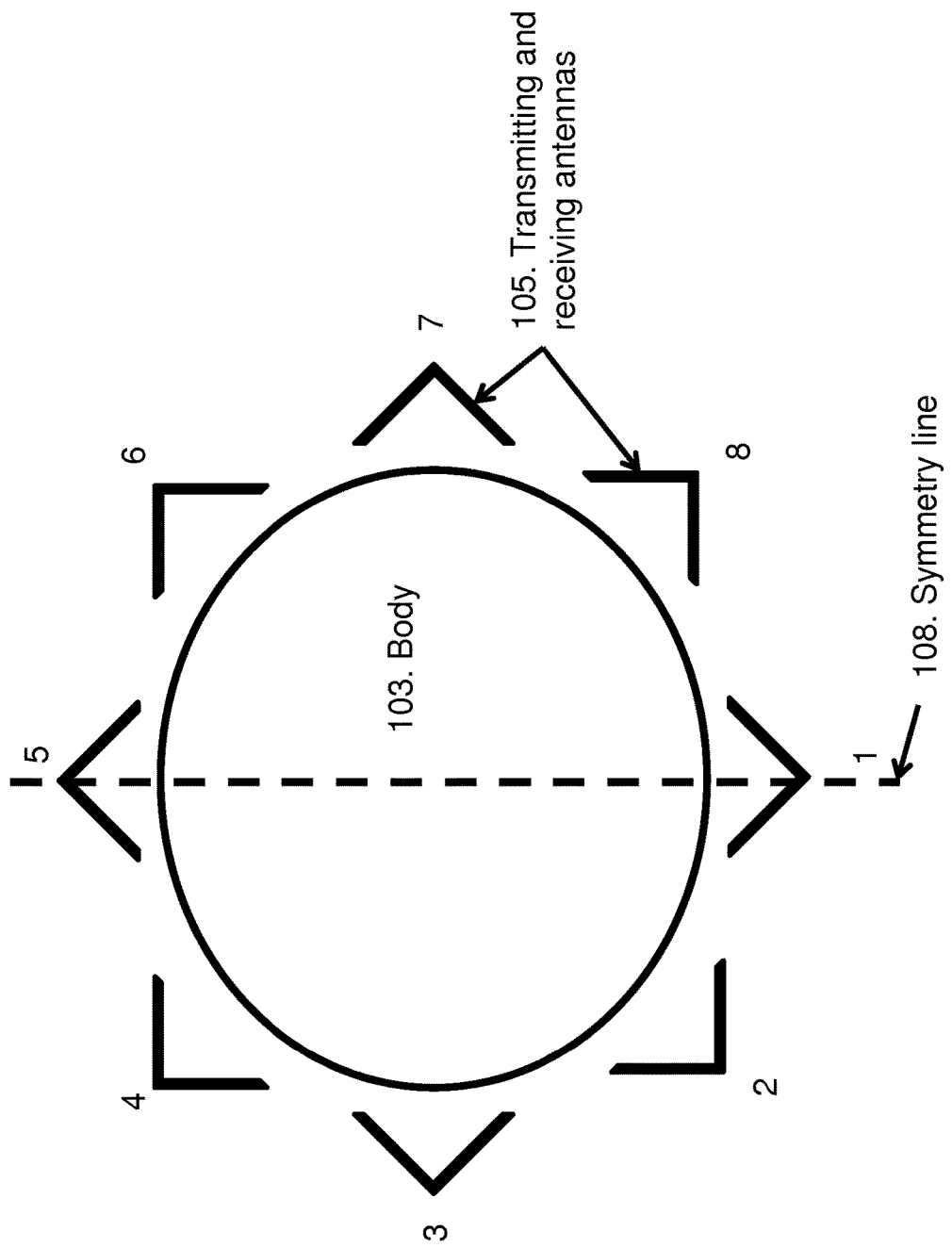
FIG. 2 is a schematic diagram illustrating an example of a system with eight antennas.

An example of the antenna configuration in the system where eight transmitting/receiving antennas 105 are adapted to be configured around the body 103 is illustrated in FIG. 2. The transmitting/receiving antennas 105 are numbered 1-8. An example of a symmetry line 108 has also been sketched in the figure. The example in FIG. 2 does not illustrate the internal object 100 to be detected.

Figure 3:
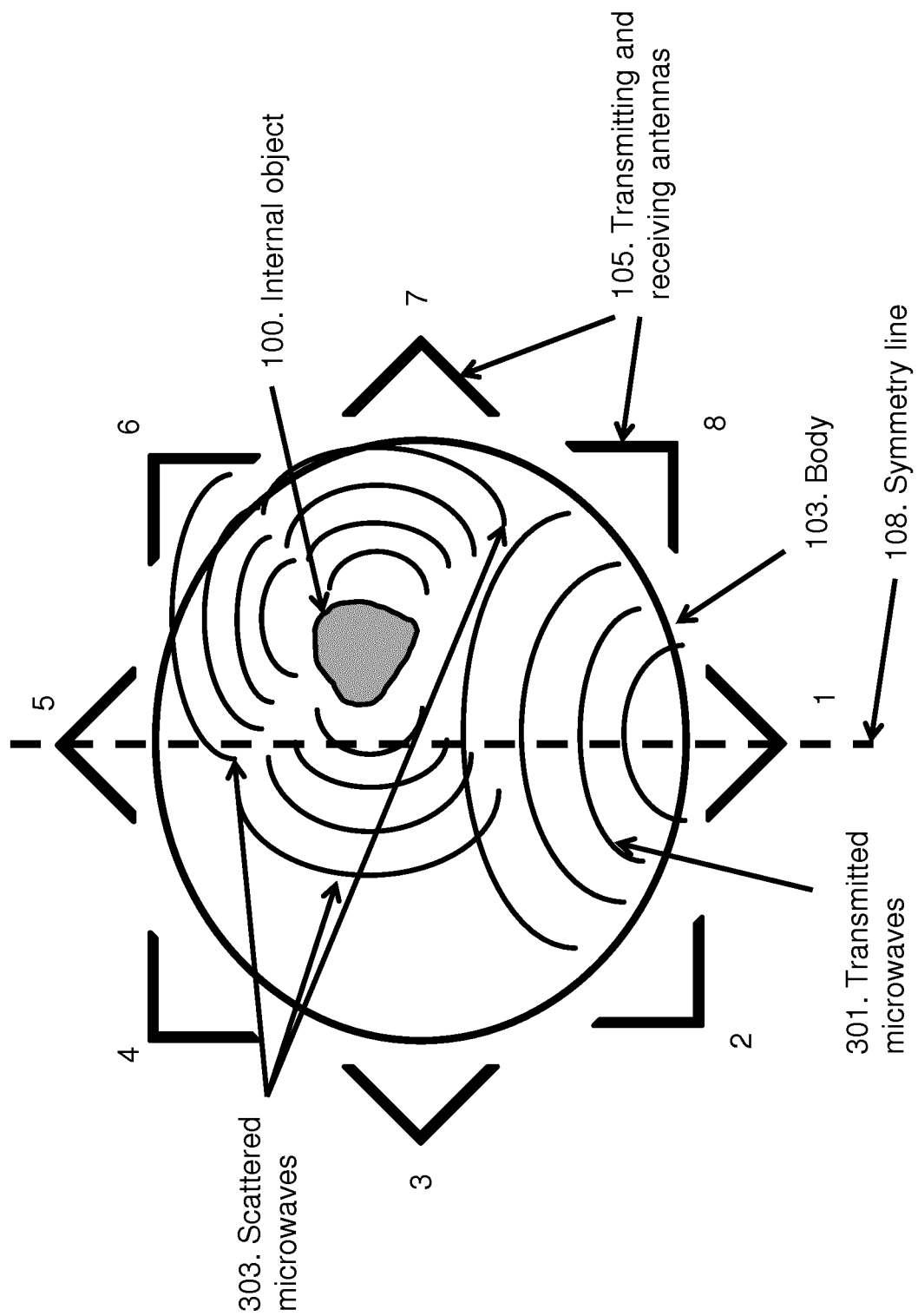
FIG. 3 is a schematic diagram illustrating an example of a system with eight antennas and where the body comprises an internal object.

FIG. 3 illustrates an example with more antennas than what is shown in FIGS. 1a-1d. Measurement strategies from all of the FIGS. 1a-1d can be adopted as the configurations of 8 antennas 105 can be arranged in multiple pairs located symmetrically around the symmetry line 108. FIG. 3 shows an example where the internal object 100 is located in the body 103. The system exemplified in FIG. 3 comprises eight antennas 105. The figure illustrates the case when one antenna 105 is transmitting microwave signals 301, the internal object 100 scatters the irradiated waves and the transmitting antenna 105 itself as well as the rest of the antennas 105 receives the scattered microwave signals 303. The internal object 100 is located asymmetrically in relation to the symmetry line 108. The embodiments herein relate to analyzing the data for asymmetries relating to the internal object 100 being detected in an otherwise symmetric or near symmetric background medium, i.e. the body 103, as seen in FIG. 3. Of the eight antennas 105, all or a subset of them can be used as transmitters and receivers and they could be operated interchangeably as pairwise transmitters and receivers. With reference to the FIG. 3 the following antenna pairs may constitute symmetric pairs when signals are transmitted from one to the other antenna 105 within the pairs:

antenna 1-antenna 2 and antenna 1-antenna 8
antenna 1-antenna 3 and antenna 1-antenna 7
antenna 1-antenna 4 and antenna 1-antenna 6
antenna 2-antenna 3 and antenna 8-antenna 7
antenna 2-antenna 4 and antenna 8-antenna 6
antenna 2-antenna 5 and antenna 8-antenna 5
antenna 2-antenna 7 and antenna 8-antenna 3
antenna 2-antenna 6 and antenna 8-antenna 4
antenna 3-antenna 4 and antenna 7-antenna 6
antenna 3-antenna 5 and antenna 7-antenna 5
antenna 3-antenna 8 and antenna 7-antenna 2
antenna 3-antenna 6 and antenna 7-antenna 4
antenna 4-antenna 5 and antenna 6-antenna 5
antenna 4-antenna 8 and antenna 6-antenna 2
antenna 4-antenna 7 and antenna 6-antenna 3

Without the internal object 100 present, antenna pairs associated to one side of the symmetry line 108 could be measured and compared with its symmetric counterpart on the other side of the symmetry line 108 and both antenna pairs should measure substantially identical received signals. In other words both antenna pairs in the symmetric combinations listed above would measure identical signals. With the internal object 100 present, one, more or all the symmetric antenna pairs would measure different received signals that could be used for detecting the presence of the internal object 100. Furthermore, in this example symmetrically positioned antennas 105 could be used to both transmit and to receive a reflected signal. The following antennas 105 may be symmetrically placed with respect to the symmetry line 108:

antenna 2 and antenna 8
antenna 3 and antenna 7
antenna 4 and antenna 6

Without the internal object 100 present in the body 103, the two antennas 105 in each pair may measure substantially identical signals. With the internal object 100 present in the body 103, one or more of the microwave signals in each pair may be different and may be used for detecting the presence of the internal object 100.

Figure 4:
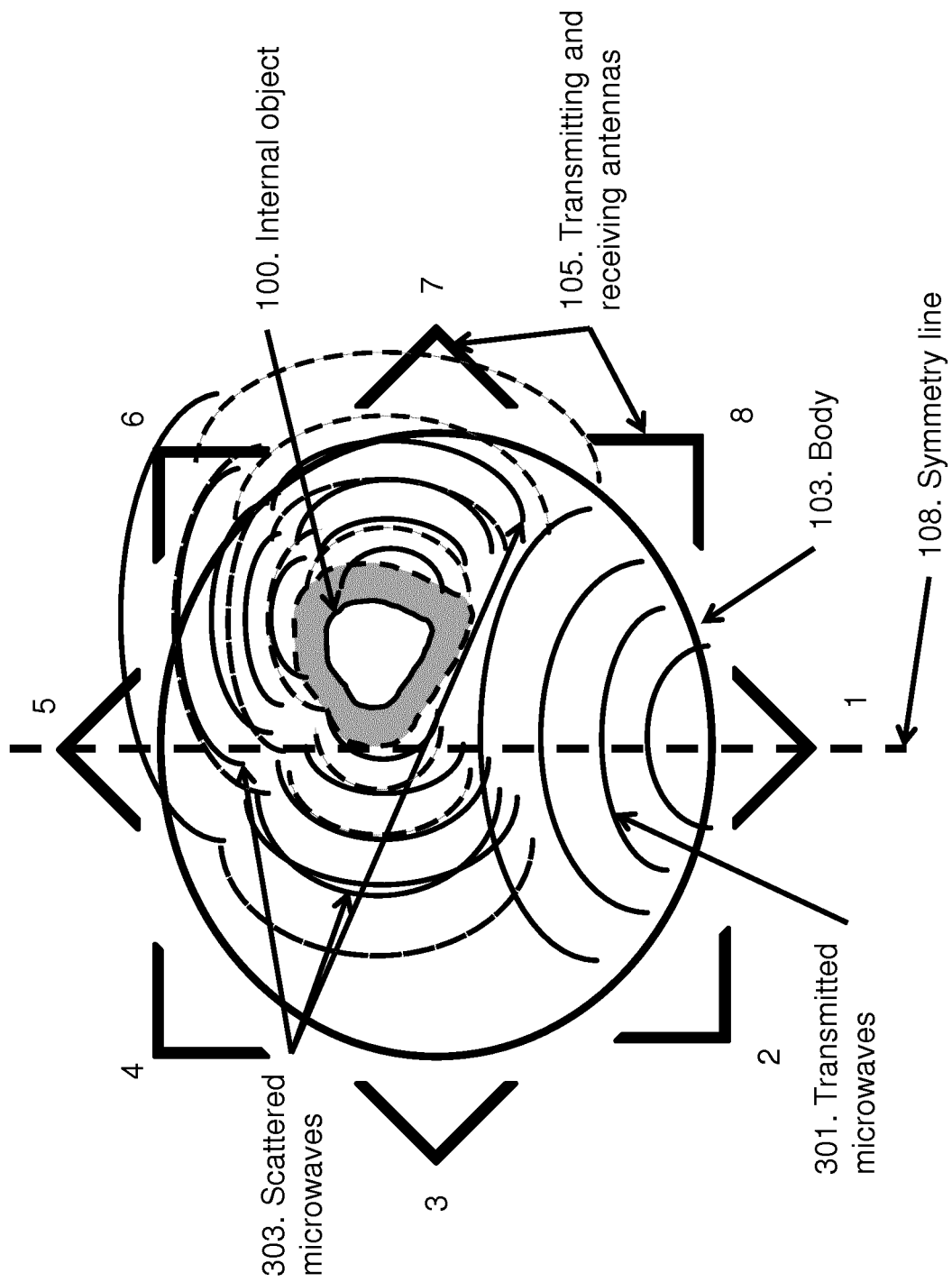
FIG. 4 is a schematic diagram illustrating an example of a system with eight antennas and where the body comprises an internal object.

FIG. 4 illustrates an example where the internal object 100 is located in the body 103. The internal object 100 is changing its properties, for example its size as illustrated here. That change causes a corresponding change in the scattered waves received by the antennas 105. The difference between the scattered microwave signals scattered from the larger and the smaller instance of the internal object 100 can be used to identify the presence of an internal object 100. The time evolution of the difference can also be used to identify and diagnose the internal object 100. By analyzing changes in asymmetries between the symmetric antenna combinations listed above further detection accuracy can be obtained in identifying and diagnosing the internal object 100.

Measurements may be collected at a single instance or repeatedly during a period of time. If data are collected at different time instances, the result will be a time series of measurement data. This way changes in the shape or properties of the internal object 100 that develop in time can be monitored.

A time series of multiple "full measurement sets" may be collected. Alternatively, a subset of the antennas 105 may be used to collect a partial measurement set. An internal object 100 that expand or shrink, change shape, or change properties during the measurements will manifest itself as causing a corresponding change in the received microwave signals and a change in the asymmetry between the symmetric antenna pairs. This change can be analyzed to determine the presence or the properties of the internal object 100.

In one embodiment, a sequence of at least two "full measurement sets" may be analyzed by an analyzer or by the system to identify and diagnose an internal object 100. If the first measurement is denoted the reference measurement, and the second measurement is differing from the reference measurement it is an indication of a change of properties of the internal object 100 between the measurements of the two "full measurement sets". Another possibility is that the second measurement is adopted to be the reference measurement, and the first measurement is differing from the reference measurement it is an indication of a change of properties of the internal object 100 between the measurements of the two "full measurement sets". The difference data can be obtained by subtracting for example S-parameter data measured at different times from the reference measurement or by subtracting pulsed data measured at different times from the reference measurement. As a result of the subtractions, a number of differential data points are obtained. Changes in time of this differential data can be related to expansion or shrinking of the internal object 100, or that it changes its shape or properties otherwise.

The reference measurement can for example be the first, last, or some other point in time when the body 103 which is under test is in a known state, e.g. the internal object 100 is not present. For a patient, this is the same as being healthy. The reference measurement could also be the patient when the clot is still present, and monitoring is made during thrombolytic treatment in order to detect when the clot has been resolved. The reference measurement could be any stable, i.e. non-changing state when the patient is healthy or non-healthy, and monitoring is made to detect if that particular state changes over time. It could either be a situation when the patient gets sicker or healthier. The reference measurement could be measured at the same or another patient at a different time or location. It can also be generated based on a simulation model or a tissue mimicking phantom.

In one embodiment, the detection of the internal object 100 may be based on the calculated differences in the received microwave signals. In another embodiment, the differential received microwave signals may be fed into a classifier. It could be the classifier described in the patent "Classification of microwave scattering data" with application number U.S. Ser. No. 13/386,521, or it could be any other classification algorithm. The differences in the received microwave signals could alternatively be fed to an image reconstruction algorithm, set up to generate a microwave tomographic image of the changes of the internal object 100.

In another embodiment this differential data can be processed by an analyzer to monitor pressure inside a body 103 being a closed cavity. If measured data change as a function of time it can be related to a change of pressure inside the body 103. An internal object 100 located inside a body 103, such as inside the skull, that expands its volume will do so by pushing away the background medium represented by the body 103. The expanding dielectric internal object 100 could be a blood volume that increases its volume as a function of time. The result is that more matter will be located inside the body 103, leading to an increased pressure inside the body 103. Such change of the amount of tissue inside the body 103 will lead to a corresponding change in the S-parameters when compared to the S-parameter data representing the reference measurement, or the corresponding pulsed time domain data when compared with the time domain representation of the reference measurement. When the internal object 100 is located asymmetrically with respect to the symmetry line 108 the received microwave signals at the symmetrically located antennas 105 will exhibit asymmetric properties or asymmetric changes in the properties.

In one embodiment this differential data is used to identify internal objects 100 that appear inside the body 103 of investigation. This could for example be a bleeding that is caused by a sudden rupture of a vessel in the brain, i.e. a stroke.

In one embodiment, an alarm may only be triggered if a change of any kind has occurred without the system making any diagnosis of what actually occurred inside the body 103 under investigation.

The sensing of an internal object 100 may be accomplished by illuminating the body 103 with electromagnetic radiation in the frequency range of microwave signals that is propagating through and scattered from the different internal objects 100. The scattered radiation is carrying the information utilized for detecting and analyzing possible abnormalities inside the body 103.

Use a series of several "full measurement sets," or subsets hereof, i.e. a sequence of "full measurement sets," or subsets, that has been collected during a period of time, to analyze asymmetries evolving as a function of time that relate to the internal object 100 and or changes in the internal object 100 being detected. For the analysis the data is divided in two subsets, relating to the two subsets of antennas 105 that are analyzed separately. The two sets are divided in relation to the symmetry line 108, see FIG. 2. An example, expressed in terms of S-parameters, of two symmetric subsets in FIG. 2 is Subset 1: $S_{23}$, $S_{24}$, $S_{34}$ and Subset 2: $S_{67}$, $S_{68}$, $S_{78}$. In general, one S-parameter may be written as $S_{ij}$, where i is the number of one of the antennas 105 in the pair and j is the number of the other antenna 105 in the pair. The definition of S-parameters is commonly known by persons skilled in the art of microwave theory and practice. S-parameters are defined in terms of incident and reflected waves at ports, (antenna ports). S-parameters are used primarily at UHF and microwave frequencies where it becomes difficult to measure voltages and currents directly. On the other hand, incident and reflected power are easy to measure using directional couplers. The definition is, $$\begin{bmatrix} b_1 \\ b_2 \end{bmatrix} = \begin{bmatrix} S_{11} & S_{12} \\ S_{21} & S_{22} \end{bmatrix} \begin{bmatrix} a_1 \\ a_2 \end{bmatrix}$$

where the $a_k$ are incident (transmitted) waves from antenna number k and $b_k$ are the waves received at port k. It is conventional to define the $a_k$ and $b_k$ in terms of the square root of power. Consequently, there is a relationship with the wave voltages at the transmitting and receiving ports, the coefficients $S_{11}$ and $S_{22}$ are denoted reflection coefficients, and $S_{12}$ and $S_{21}$ transmission coefficients. For reciprocal systems, like the case for us, $S_{12}$=S21. And for symmetric systems $S_{11}$=$S_{22}$.

If data from symmetric antenna pairs 105 are subtracted from each other the residual will ideally be zero in a completely symmetric antenna configuration and with a symmetric internal object 100 inside the setup.

That means for example: $^{sym}S_{23}$-$^{sym}S_{67}$=0, $^{sym}S_{24}$-$^{sym}S_{68}$=0, $^{sym}S_{34}$-$^{sym}S_{78}$=0.

In an example with real measurement data, perfect symmetry is not achievable, either because the antenna configuration is not completely symmetric, or because the body 103 is not perfectly symmetric, for example due to manufacturing tolerances or the body 103 not being perfectly symmetric. In all cases the residual will be close to zero and can come arbitrarily close to zero if the system or the body 103 is made more symmetric, e.g. if the manufacturing tolerances are made smaller or by calibration methods. That means for example:

$|^{approx\ sym}S_{23}$-$^{approx\ sym}S_{67}|=\|\|_{23\text{-}67}$,
$|^{approx\ sym}S_{24}$-$^{approx\ sym}S_{68}|=\|\|_{24\text{-}68}$,
$|^{approx\ sym}S_{34}$-$^{approx\ sym}S_{78}|=\|\|_{34\text{-}78}$, and with $\|\|_{x\text{-}y}$ becoming smaller the more perfectly symmetric the body 103, where x and y are positive integers and represents the number of the antenna pairs. This may be called asymmetry data. Approx. is short for approximation.

If an internal object 100 is located asymmetrically in the body 103, in the otherwise symmetric system, the residual is nonzero. If the magnitude of the residual with asymmetrically placed dielectric internal object 100 is larger than the magnitude of the residual for an empty body 103, the residual can be used as an indicator of detection.

That is for example if $|^{assym\ obj}S_{23}$-$^{assym\ obj}S_{67}|=\|\|_{23\text{-}67}|$,
$|^{assym\ obj}S_{24}$-$^{assym\ obj}S_{68}|=\|\|_{24\text{-}68}|$,
$|^{assym\ obj}S_{34}$-$^{assym\ obj}S_{78}|=\|\|_{34\text{-}78}|$, with the asymmetric internal object 100 present during collection microwave signals that are represented in form of S-parameters.

This asymmetry in the data is manifested as a difference in the transmission and reflection data, for example but not limited to, asymmetry in the S-parameters, asymmetry in the received pulsed data, or asymmetry in the received p-n sequence data.

The transmission data and reflection data used can be the complex transmission and reflection data. It could also be the magnitude of the transmission and reflection data or the phase of the transmission and reflection data.

If the above asymmetry in the data is changing in time it indicates that the dielectric internal object 100 is changing its size and/or position during a set of measurements. This can be used as a detection/monitoring criteria. Examples could be that an initially symmetric data becomes non-symmetric as a dielectric internal object 100 appears asymmetrically. This could for example be a bleeding 100 in the head 103 that is caused by a sudden rupture of a vessel and where the volume of blood gradually increases. It can also be a situation where initially the data is asymmetric, and where it as time evolves becomes more or less asymmetric.

An asymmetry measure can be achieved by integrating the asymmetry data over a specified frequency range that could be the whole or part of the frequency range over which the measurement is performed. The specified frequency range is $f_{stop}$-$f_{start}$, where $f_{start}$ and $f_{stop}$ are the beginning and end of the integration. $f_{start}$ is the frequency for the start of the measurement and $f_{stop}$ is the frequency of the stop of the measurement. The frequency is measured in Hertz (Hz).

The measured microwave signals can be corrected for intrinsic asymmetries of the transmitting and receiving antennas 105, for example if the antennas have different orientation. This can be achieved for example by subtracting the asymmetry measure obtained from measurements on one or more symmetric bodies 103 from the corresponding asymmetry measures obtained when making a measurement to identify an internal object 100. Alternatively, it can be done by subtracting transmission signals and reflection signals obtained from one or more symmetric bodes 103 from the corresponding asymmetry measures obtained when making a measurement to identify an internal object 100.

The asymmetry measure obtained for each set of discrete $f_{start}$ and $f_{stop}$ values can be combined in to matrix form where for example the rows correspond to different $f_{start}$ values and the columns corresponds to different $f_{stop}$ values.

The asymmetry measure matrix then obtained can be used to evaluate the asymmetry in different ways. An example of such evaluation is to add all the elements in the matrix to a single total asymmetry measure. Another way is to feed the different elements into a classifier in order to determine which class the internal object 100 corresponds to.

For a set of several bodies 103, e.g. a set of different patients that are measured, there will be a set of asymmetry measure matrices. In one embodiment, the S-parameter data, or any other form of the data, is normalised before the analyzis. There are different ways to normalise this set of asymmetry measure matrices. One such normalisation is done so that the total received power in each antenna 105 is made equal for all measurements. That could for example be realized such that the transmission coefficients are normalized such that they are equal in amplitude.

Another such normalisation is one where the total power entering all bodies 103 are equal. That could for example be realized such that the reflection coefficients are equal in amplitude.

Yet another such normalisation is such that the maximum total individual asymmetry measure among the set of bodies 103 are set to unity. For example:
Max ($|{}^{assym\ obj}S_{23}$-${}^{assym\ obj}S_{67}|$, $|{}^{assym\ obj}S_{24}$-${}^{assym\ obj}S_{68}|$, $|{}^{assym\ obj}S_{34}$-${}^{assym\ obj}S_{78}|$)=1.

The embodiments herein relate to analyzing the data in order to detect differences in transmission and reflection data relating to differences in dielectric properties of bodes 103 being studied. One way to analyze the data is to divide the antennas 105 into one or more pairs that are positioned around the body 103.

Time resolved data, i.e. a sequence of "full measurement sets" may be used to analyze transmission that relate to the internal object 100 being detected. This may be called the transmission data. This difference between different bodies 103 measured is manifested as a difference in the transmission and reflection data.

The transmission data and reflection data used can be the total complex transmission and reflection data. It could also be the magnitude of the transmission and reflection data or the phase of the transmission and reflection data.

If the above transmission data is changing in time it indicates that the dielectric internal object 100 is changing its size and/or position during a set of measurements. This can be used as a detection/monitoring criteria.

A transmission measure can be achieved by integrating the transmission data over a specified frequency range that could be the whole or part of the frequency range over which the measurement is performed.

The specified frequency range is $f_{stop}$-$f_{start}$, where $f_{start}$ and $f_{stop}$ are the beginning and end of the integration.

The transmission measure obtained for each set of discrete $f_{start}$ and $f_{stop}$ values can be combined into matrix form where for example the rows correspond to different fstart values and the columns corresponds to different $f_{stop}$ values.

The transmission measure matrix then obtained can be used to evaluate the internal object 100 in different ways. An example of such evaluation is to add all the elements in the matrix to a single total transmission measure. Another way is to feed the different elements in to a classifier in order to determine which class the internal object 100 corresponds to. It could be the classifier described in the patent "Classification of microwave scattering data" with application number U.S. Ser. No. 13/386,521, or it could be any other classification algorithm.

For a set, e.g. two or more, of internal objects 100 there will be a set of transmission measure matrices. There are different ways to normalise this set of transmission measure matrices. One such normalisation so that total received power equal for all subjects. Another such normalisation is one where the total power entering all individuals is equal.

Another such normalisation is such that the maximum total individual transmission measure among the set of individuals are set to unity.

As mentioned earlier, all antennas 105 the antenna pair of the system may be positioned with the same angle. Such system may be referred to as a symmetric system. In another example, the antennas 105 in different pairs are positioned with different angles, i.e. the antennas 105 inside a pair have the same angle and the antennas in different pairs have different angles. Such system with different angles may be referred to as an asymmetric system. The symmetric and asymmetric system will now be shortly described:

Symmetric System

All antennas 105 in the system are positioned symmetrically around the body 103, and they are positioned with the same angle or orientation with respect to the body 103, e.g. the surface of the body 103. Initially it is assumed that the body 103 does not have any internal object 100 and is therefore a substantially symmetric body 103. The measured signals in the symmetric body 103 are consequently also symmetric. Symmetric signals may be an indication of a healthy body 103, i.e. a body 103 without the internal object 100 present. This could for example represent a healthy person. When measurements are performed at a later time, and the measured signals are asymmetric signals, it is an indication of that an internal object 100 has been detected in the body 103. The body 103 is no longer symmetric and has become an asymmetric body 103 due to the internal object 100. The signal change over time indicates the presence of the internal object 100. This could for example represent a patient with a haemorrhage in the head, where the patent's head is the body 103 and the haemorrhage is the internal object 100.

Asymmetric System

All antennas 105 in the system are positioned symmetrical around the body 103. The antennas 105 in one pair is positioned with an angle or orientation with respect to the body 103 which is different from the angle in which antennas 105 in another pair is positioned with respect to the body 103. Initially it is assumed that the body 103 does not have any internal object 100 and is therefore a substantially symmetric body 103. However, the measured signals in the symmetric body 103 in the asymmetric system are asymmetric due to the different angles of the antenna pairs. Asymmetric signals may therefore in this case be an indication of a healthy person, even though no internal object 100 has been detected. When measurements are also performed at a later time, and the measured signals still are asymmetric signals but the asymmetry measures have changed, it is an indication of that an internal object 100 has been detected in the body 103 due to time changes in the asymmetric signals.

Figure 5:
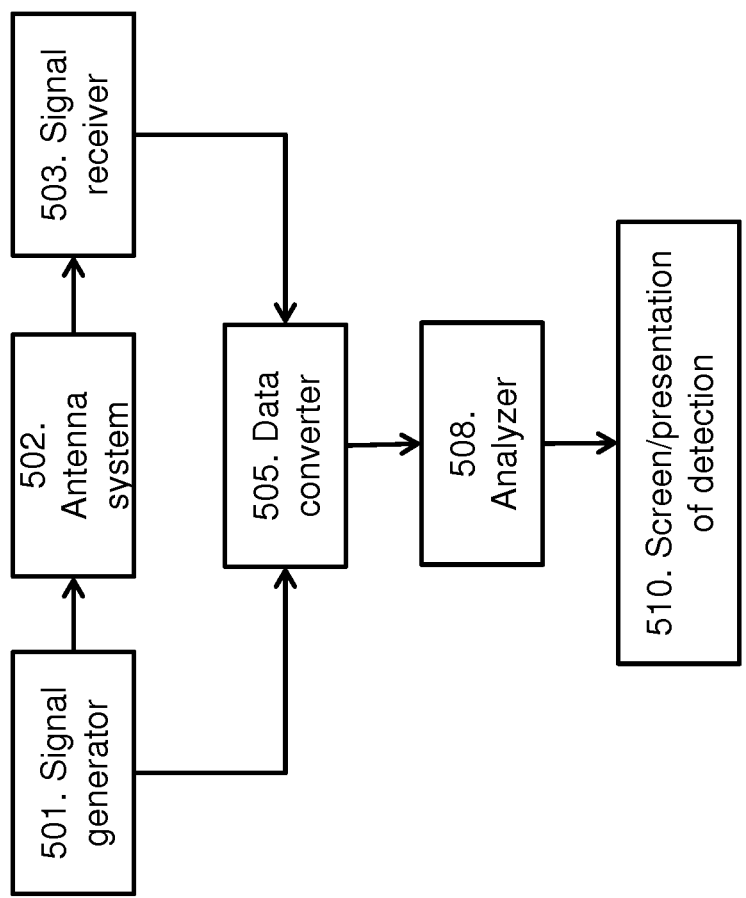
FIG. 5 is a schematic diagram illustrating an example of a system.

FIG. 5 illustrates an example of a system comprising at least one of: a microwave signal generator 501, an antenna system 502 and a signal receiver 503, both connected to form the system, used to collect data. The received microwave signals may be seen as the basis for a data converter 505 which calculates or coverts the received microwave signals in to a data representation, e.g. S-parameters. The data representation of the received microwave signals, e.g. the S-parameters, may be fed to an analyzer 508 where the detection of the object 100 may be made. The result may be presented for example but not limited to a screen 510 or in monitoring applications. Also, an alarm may be triggering in order to alert staff. The alarm may be at least one of: an audio alarm, a visual alarm, a haptic alarm or any other suitable alarm type with the purpose of informing a user of the system about the detected internal object 100 or a change in the internal object 100.

The system exemplified in FIG. 5 comprises a signal generator 501, an applicator, i.e. the system, an antenna system 502, a signal receiver 503, a converter 505, an analyzer 508 and a screen or a different device 510 for presenting the result. The antennas 105 in the system transmit and receive microwave signals. The measured microwave signals collected for instance from continuous microwave signals measured at single or multiple discrete frequencies, or from pulsed or p-n sequence microwave signals. The microwave signals are spanning a given and pre-defined frequency range. The frequency range is for example but not limited to 100 MHz to 10 GHz or more. The frequency interval can be narrower but also wider. Based on the measured microwave signals, transmission and/or reflection data, for example but not limited to S-parameter data are calculated in the data converter 505. S-parameter data, or other representations of the measured data, are calculated from the transmitted and/or received microwave signals and then fed to the analyzer 508. Other representations of the microwave signal is in form of z-, y-, h-, t-parameter or ABODE-parameters, reflection coefficients, insertion loss, a percentage parameter, a magnitude parameter, a phase parameter, a time-domain pulse or any other representation of the received microwave signal. These different representations of microwave signals are well known to persons skilled in the art of microwave theory and practice. The result from the analyzer is presented on a screen or some other relevant device 510.

The system may be seen as to constitute the interface between the microwave system and the body 103, and it consists of at least one transmitter of microwave signals, e.g. an antenna 105, that is adapted to be placed outside the body 103 and arranged to send microwave signals into the body 103. The antennas 105 transmitting and receiving the microwave signals may be connected to a signal generator 501 and a signal receiver 503 respectively. One or more signal receivers 503 may be adapted to be located outside the body 103 and detects the scattered radiation which is later processed by an algorithm for data analyzis and diagnosis.

In some embodiments, one or more of the signal generator 501, the signal receiver 503, the data converter 505, the analyzer 508 and the screen 510 may be incorporated into the system, e.g. one of the antennas 105 in the system. In another embodiment, all modules illustrated in FIG. 5 are separate standalone modules. In a further embodiment, some of the modules illustrated in FIG. 5 may be co-located with each other, for example, the data converter 505 and the analyzer 508 may be co-located in one module and the signal-generator 501 and the system may be co-located in one module. The analyzer 508 may be for example a processor. In addition, the system may comprise at least one memory (not shown in FIG. 5) which is adapted to store the measured signals.

Some embodiments described herein may be summarised in the following manner:

A system for detecting an internal object 100 in a body 103. The internal object 100 and the body 103 have different dielectric properties. The system comprises at least one antenna pair comprising two antennas 105 which are adapted to be symmetrically positioned around the body 103 in relation to a line of symmetry 108 in the body. The system being adapted to:

Transmit one microwave signal or multiple microwave signals into the body 103 from at least one of the antennas 105 in the system. The transmitted microwave signals are reflected and/or scattered from the internal object 100.

Receive the reflected and/or scattered microwave signals at the other antenna 105 and/or at the transmitting antenna 105 whereby it is operated as a receiver after it has transmitted or it is operated as a receiver at the same time as it is transmitting.

Compare the received microwave signals at the symmetrically positioned antennas 105.

Detect the internal object 100 or a change in an already detected internal object 100 when there is a difference between the received microwave signals at symmetric antenna pairs. The difference is related to the different dielectric properties between the internal object 100 and the body 103.

The system may be further adapted to determine a type of the internal object 100 or properties of the internal object 100 based on the difference between the received microwave signals at symmetric antenna pairs related to the different dielectric properties and their spatial distribution.

The system may be further adapted to provide, to a user of the system, information associated with the detected internal object or the change in the already detected internal object 100.

The microwave signals may be transmitted from all antennas 105 in the system or from a symmetrically positioned subset of the antennas 105 in the system.

The system may be further adapted to obtain a representation of the received microwave signal. The representation of the received microwave signal may be used when comparing the received microwave signals. The representations of the received microwave signal at each receiver antenna 105 may be normalized with a common normalization factor before analyzing and comparing the received microwave signals The representation of the received microwave signal may be in the form of pairs of a S-, z-, y-, h-, t-parameter or ABCDE-parameters, reflection coefficients, insertion loss, a percentage parameter, a magnitude parameter, a phase parameter, a time-domain pulse or any other representation of the received microwave signal.

The received microwave signals may be received for all or a subset of symmetric antenna pairs for a single instance in time or for several instances during a period of time.

The difference between the received microwave signals at symmetric antenna pairs during a period of time may be analyzed and may be used to detect presence or change of properties of the internal object 100.

The system may be further adapted to determine that there is no internal object 100 in the body 103 when there is not any difference between the received microwave signals at symmetrically positioned antennas in the pair.

The two antennas 105 in the antenna pair may be adapted to be symmetrically positioned around the body 103 in relation to the line of symmetry 108 in the body 103 so that one antenna 105 is at a first position on one side of the line of symmetry 108 and the other antenna 105 is at a corresponding and symmetric second position on the other side of the line of symmetry 108. The first and second position may be symmetrical positions on each side of the line of symmetry 108.

One antenna in an antenna pair may be common between the two pairs where the common antenna 105 may be adapted to be positioned on the symmetry line 108 and where the remaining antennas 105 may be adapted to be symmetrically positioned around the body 103 in relation to the line of symmetry 108 in the body 103 so that one antenna 105 is at a first position on one side of the line of symmetry 108 and the other antenna 105 is at a corresponding and symmetric second position on the other side of the line of symmetry 108. The first and second position may be symmetrical positions on each side of the line of symmetry 108.

The two antennas 105 in the antenna pair may be adapted to be positioned with the same angle in relation to the line of symmetry.

The body 103 may initially be a substantially symmetric body and the internal object (100) may be asymmetrically located in the substantially symmetric body 103. The term substantially may refer to that there is some tolerance when it comes to how symmetric the body 103 may be. The body may initially be an asymmetric body and the internal object 100 may be asymmetrically located in the asymmetric body 103.

The internal object 100 or the change in the already detected internal object 100 may be detected when the difference between the received microwave signals are equal to or above a threshold. No internal object 100 or no change in the already detected internal object 100 may be detected when the difference between the received microwave signals at symmetric antenna pairs is below the threshold.

The antennas may be adapted to be symmetrically positioned and asymmetrically oriented, and differences as a function of time may be indicative of the presence of an internal object 100.

The transmitted microwave signals may be in the frequency range of 100 MHz-10 GHz or the range of 100 MHz to 10 GHz or the range of 100 MHz to 5 GHz.

The body 103 may be a human body part, an animal body part, it may be made of biological tissue, wood, plastic or any other non-organic or organic material.

The internal object 100 may be solid, semisolid, liquid or gas.

The internal object 100 may represent a bleeding, a clot, an ongoing bleeding, a reoccurring bleeding, a tumour, a malignant lesion, a haemothorax, a pneumothorax, a defect in wood, a knot, a nail, a tree rot, an impurity or any internal object with different dielectric properties than the body 103.

A method performed by a system for detecting an internal object 100 in a body 103. The internal object 100 and the body 103 have different dielectric properties. The system comprises at least one antenna pair comprising two antennas 105 which are adapted to be symmetrically positioned around the body 103 in relation to a line of symmetry in the body 103. The method comprises at least one of the following steps, which steps may be performed in any suitable order than described below:

Transmitting one or a plurality of microwave signals into the body 103 from at least one of the antennas 105. The transmitted microwave signals is reflected and/or scattered from the internal object 100.

Receiving the reflected and/or scattered microwave signals at the other antenna 105 and/or at the transmitting antenna 105 whereby it is operated as a receiver after it has transmitted or it is operated as a receiver at the same time as it is transmitting.

Comparing the received microwave signals at the symmetrically positioned antennas 105.

Detecting the internal object 100 or a change in an already detected internal object 100 when there is a difference between the received microwave signals at symmetric antenna pairs, and wherein the difference is related to the different dielectric properties between the internal object 100 and the body 103.

The method may further comprise:

Determining a type of the internal object 100 or properties of the internal object 100 based on the difference between the received microwave signals at symmetric antenna pairs related to the different dielectric properties and their spatial distribution.

The method may further comprise:

Providing, to a user of the system, information associated with the detected internal object or the change in the already detected internal object 100.

The microwave signals may be transmitted from all antennas 105 in the system or from a symmetrically positioned subset of the antennas 105 in the system.

The method may further comprise:

Obtaining a representation of the received microwave signal. The representation of the received microwave signal may be used when comparing the received microwave signals.

The representation of the received microwave signal at each receiver antenna 105 may be normalized with a common normalization factor before analyzing and comparing the received microwave signals.

The representation of the received microwave signal may be in the form of pairs of a S-, z-, y-, h-, t-parameter or ABCDE-parameters, reflection coefficients, insertion loss, a percentage parameter, a magnitude parameter, a phase parameter, a time-domain pulse or any other representation of the data.

The received microwave signals are received for all or a subset of symmetric antenna pairs for a single instance in time or for several instances during a period of time.

The difference between the received microwave signals at symmetric antenna pairs during a period of time may be analyzed and may be used to detect presence or change of properties of the internal object 100.

The method may further comprise:

Determining that there is no internal object 100 in the body 103 when there is not any difference between the received microwave signals at symmetrically positioned antennas 105 in the pair.

The two antennas 105 in the antenna pair may be symmetrically positioned around the body 103 in relation to the line of symmetry 108 in the body 103 so that one antenna 105 is at a first position on one side of the line of symmetry 108 and the other antenna 105 is at a corresponding and symmetric second position on the other side of the line of symmetry 108. The first and second position may be symmetrical positions on each side of the line of symmetry 108.

One antenna 105 in an antenna pair may be common between two antenna pairs. The common antenna 105 may be adapted to be positioned on the symmetry line 108 and the remaining antennas 105 may be adapted to be symmetrically positioned around the body 103 in relation to the line of symmetry 108 in the body 103 so that one antenna 105 is at a first position on one side of the line of symmetry 108 and the other antenna 105 is at a corresponding and symmetric second position on the other side of the line of symmetry 108. The first and second position may be at symmetrical positions on each side of the line of symmetry 108.

The two antennas 105 in the antenna pair may be positioned with the same angle in relation to the line of symmetry.

The body 103 may be initially a substantially symmetric body and the internal object 100 may be asymmetrically located in the substantially symmetric body 103, or the body 103 may be initially an asymmetric body and the internal object 100 may be asymmetrically located in the asymmetric body 103.

The internal object 100 or the change in the already detected internal object 100 may be detected when the difference between the received microwave signals are equal to or above a threshold. No internal object 100 or no change in the already detected internal object 100 may be detected when the difference between the received microwave signals at symmetric antenna pairs is below the threshold.

The antennas 105 may be symmetrically positioned and asymmetrically oriented, and where differences as a function of time may be indicative of the presence of an internal object.

The transmitted microwave signals may be in the frequency range of 100 MHz-10 GHz.

The body 103 may be a human body part, an animal body part, it may be made of biological tissue, wood, plastic or any other non-organic or organic material. The internal object 100 may be solid, semisolid, liquid or gas.

The internal object 100 may represent a bleeding, a clot, an ongoing bleeding, a reoccurring bleeding, a tumor, a malignant lesion, a haemothorax, a pneumothorax, a defect in wood, a knot, a nail, a tree rot, an impurity or any internal object with different dielectric properties than the body 103.

A computer program may comprising instructions which, when executed on at least one processor, cause the at least one processor to carry out the method described above. A carrier may comprise the computer program, and the carrier may be one of an electronic signal, optical signal, radio signal or computer readable storage medium.

An antenna system comprises at least one antenna pair comprising two antennas 105 which are adapted to be symmetrically positioned around the body 103 in relation to a line of symmetry in the body 103. In other words the antennas described above in relation to the system may be the antennas in the antenna system. Thus, the system may comprise the antenna system. The antenna system may be the antenna system 502 illustrated in FIG. 5. The antenna system is adapted to:

Transmit one or multiple microwave signals into a body 103 from at least one of the antennas 105 in the pair. The transmitted microwave signals is reflected and/or scattered from an internal object 100 in the body 103.

Receive the reflected and/or scattered microwave signals at the other antenna 105 and/or at the transmitting antenna 105 whereby it is operated as a receiver after it has transmitted or it is operated as a receiver at the same time as it is transmitting.

Provide information associated with the received microwave signals to an analyzing unit.

Other examples of applications for the embodiments herein are for various monitoring applications. It could be monitoring of patients with an increased risk of getting a stroke. Monitoring could be made during sleep or while the patient lies down in bed, or with compact wearable systems during daytime. If the system detects an occurrence of a stroke it will immediately trigger an alarm to alert that a stroke has occurred, and also immediately give a diagnosis whether it was a bleeding or a clot. It could also be used for monitoring of patients that undergo thrombolytic treatment. In this case, it is of interest to monitor if the treatment is effective, the clot resolved and the circulation restored. In patients with a bleeding stroke the system could be used for monitoring if the bleeding is ongoing or if it has stopped. In patients that have had a bleeding it could be used to detect if the bleeding starts over. There exist also a number of other monitoring situations where it is of interest to monitor the occurrence, presence, or changes in a present bleeding, or other types of liquids, e.g. edemas, in the skull where a wearable version of the system could give a detection and a diagnosis. Applications, such as bedside intracranial monitoring will be possible where the pressure is coupled to the amount of liquid inside the skull.

The embodiments herein could also be used in other conditions, such as pre-hospital diagnostics of traumatic brain injury patients or monitoring of various conditions in the head at the neuro intensive care, or in other similar applications. It would also be possible to apply the embodiments herein to diagnostics of other parts of the human body, e.g. the abdomen in case of suspected internal bleeding or the thorax for detection of pneumothorax or hemothorax. In that case, the system has to be suitably designed but the analyzis could be done with the same equipment as for the brain applications.

The embodiments herein provide additional information and at an earlier time in the chain of care compared to the current system. This makes it possible to distinguish between healthy people and stroke patients, and further to diagnose between ischemic and hemorrhagic stroke. Deployed for example in ambulances, or in any pre-hospital setting, or at the arrival point of ambulances at hospitals, embodiments herein facilitate earlier diagnosis and thus enable earlier treatment.

One area of application for the embodiments herein is in diagnosing stroke patients by means of a system that can be used in an ambulance or a pre-hospital setting for assessments of patients with suspected stroke. The system could also be used at the hospital for assessment of patients with suspected stroke. The embodiment herein helps to reduce the time from the occurrence of the stroke till the time of making a correct diagnosis of the stroke.

In one embodiment, the system is setup to generate microwave signals and take measurements that are used to calculate, for example but not limited, to S-parameter data in the desired frequency range between the transmit-receive antenna combinations. Other examples of representations of the measurement data could be z, y or h-parameters, reflection coefficients, insertion loss, etc. Data can be collected at one or more frequencies in the range. Data collected in time-domain or in frequency domain are both related by the Fourier Transformation. From a point of data analyzis, the two different sets of data are of equal value. The measurement electronics for frequency domain measurements, or pulsed measurements differ.

Necessary information may be extracted from the measured data, represented for example as the calculated S-parameter data, and processed with an algorithm in order to perform the detection of the internal object 100. This may be done by one of the antennas 105, an analyzer in one of the antenna 105, an external analyzer or any other suitable unit. The detections are based on a dielectric contrast between the internal object 100 that is being detected and the body 103 in which the internal object 100 is located. The internal object 100 that is detected could be a gas, liquid, a solid or a semisolid substance that is immersed inside another dielectric object, i.e. the body 103. The body 103 and the internal object 100 should have different dielectric properties in order to create a detectable contrast. The dielectric properties may be apparent in the presence of microwave signals.

To improve data quality in terms of, for example but not limited to, signal to noise ratio, several full measurement sets after each other could be measured. The data quality of the data could then be improved for example by averaging.

The embodiments described herein detects and monitors of dielectric internal objects 100 by microwave tomography utilizing the dielectric contrasts between the different parts of objects, i.e. the internal object 100 and the body 103, and the effects that has on the measured data.

The embodiments herein detects and monitors dielectric internal objects 100 in a body 103 by classification utilizing the differences in the dielectric contrasts between the different classes of objects 100 and their effects on the measured data. It could be the classifier described in the patent "Classification of microwave scattering data" with application number U.S. Ser. No. 13/386,521, or it could be any other classification algorithm.

The detection and monitoring of dielectric internal objects 100 that are, for example but not limited to, expanding, decreasing its size, changing its shape, or changing its properties or moving while the measurements are ongoing.

The internal object 100 may be manifested in the measurements in terms of the transmission and reflection data, for example but not limited to, the S-parameters, the received pulsed data, or the received p-n sequence data.

Microwave techniques can provide non-invasive, easy access, to the human brain at a relatively low cost providing a large amount of multi frequency scattering data that can be used to analyze the continues developments of the dielectric and geometric properties of the human brain. An imaging modality for traumatic brain injury patients may allow for a continuous bedside brain imaging system. The embodiments herein include monitoring of other parts of the body 103, e.g. trunk, abdomen and extremities, in case of suspected internal bleeding. In that case the system is suitably designed but the analyzis could be done with the same equipment as for the brain monitoring.

In such system, electromagnetic radiation in the microwave region is injected into the body with the help of an antenna 105. Other antennas 150 are used to receive the radiation after it has propagated through the head. On its way through the body 103 the waves have been affected by the internal objects 100 and thus bear information about the tissue or material they propagated through.

The embodiments herein are directed towards the estimation of an internal condition in an enclosed volume. The internal condition is represented by the internal object 100 and the enclosed volume is represented by the body 103. A few example applications have been presented above, such as medical diagnosis for obtaining information about internal objects 100 of human or animal body 103. However, one of skill in the art would appreciate that the example embodiments discussed may be used in any type of application utilizing microwave scattering data for the purpose of monitoring, detection, and/or diagnosis. For example, the embodiments presented herein may be utilized for various bodies 103 such as trees, buildings, etc. Various different types of internal objects 103 may be monitored, for example, the presence of a particular liquid 100 in the enclosed volume 103. The body 103 may be a patient and the internal object 100 may represent a medical condition, which manifests itself as a dielectric contrast with respect to the healthy tissue comprised in the body 103. The body 103 may also be a tree and the internal object 100 may represent tree health, which manifests itself as a dielectric contrast with respect to the healthy wood. In principle, all internal conditions of a body 103 which can be expressed as a dielectric contrast, where the dielectric properties of the internal condition is different from the healthy or normal background tissue.

The various embodiments described herein is described in the general context of method steps or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), USB, Flash, HD, Blu-Ray, etc. Generally, program modules may include routines, programs, objects, components, data structures, etc. that performs particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The embodiments herein are not limited to the above described embodiments. Various alternatives, modifications and equivalents may be used. Therefore, the above embodiments should not be taken as limiting the scope of the embodiments, which is defined by the appending claims. A feature from one embodiment may be combined with one or more features of any other embodiment.

It should be emphasized that the term "comprises/comprising" when used in this specification is taken to specify the presence of stated features, integers, steps or components, but does not preclude the presence or addition of one or more other features, integers, steps, components or groups thereof. It should also be noted that the words "a" or "an" preceding an element do not exclude the presence of a plurality of such elements. The terms "consisting of" or "consisting essentially of" may be used instead of the term comprising. Several "means" or "units" may be represented by the same item of hardware.

The term "configured to" used herein may also be referred to as "arranged to", "adapted to", "capable of" or "operative to".

It should also be emphasised that the steps of the methods defined in the appended claims may, without departing from the embodiments herein, be performed in another order than the order in which they appear in the claims.

The invention claimed is:

1. A system for detecting an internal object in a body, the internal object and the body having different dielectric properties, the body being initially substantially symmetric and having a symmetry line which represents a division of the body in two body parts that are counterparts, each of the body parts on a respective side of the symmetry line being substantially symmetric in shape, each of the body parts on the respective side of the symmetry line being initially substantially symmetric in content when no internal object is located in the body, the internal object being asymmetrically disposed with respect to the symmetry line of the body when the internal object is located in the body, the system comprising:
at least one antenna pair comprising two antennas configured to be positioned directly opposite one another in relation to the body and on opposite sides of the symmetry line in the respective counterparts of the body such that one of the antennas in the antenna pair is configured to be symmetrically positioned around the body with respect to the other antenna in the antenna pair and in relation to the symmetry line,
wherein the system is configured to:
transmit at least one microwave signal into the body from at least one of the antennas, the at least one transmitted microwave signal being reflected and/or scattered from the internal object,
receive reflected and/or scattered microwave signals at one or more of: (i) the other antenna and (ii) the transmitting antenna, whereby the one or more of the other antenna and the transmitting antenna is operated as a receiver after the transmitting antenna transmits the at least one microwave signal or the one or more of the other antenna and the transmitting antenna is operated as a receiver at the same time as the one or more of the other antenna and the transmitting antenna is transmitting,
compare the received microwave signals at the symmetrically positioned antennas, and
detect, based on an analysis of one or more of: (i) a plurality of asymmetries, and (ii) changes in asymmetries in the received microwave signals, the internal object or a change in an already-detected internal object when there is a difference between the received microwave signals at symmetric antenna pairs, the asymmetries including asymmetries in received p-n sequence data of the received microwave signals, the difference being related to the different dielectric properties between the internal object and the body,
wherein the body is one of a head, a brain, an abdomen, a thorax, and a leg, and
wherein the antennas of each of the at least one antenna pair are directly opposite one another with respect to the body on a plane passing through the body and perpendicular to the symmetry line.

2. The system according to claim 1, wherein the difference between the received microwave signals at symmetric antenna pairs during a period of time is analyzed and is used to detect a presence or a change of properties of the internal object.

3. The system according to claim 2, wherein the internal object or the change in the already-detected internal object is detected when the difference between the received microwave signals is equal to or above a threshold, and
wherein no internal object or no change in the already detected internal object is detected when the difference between the received microwave signals at symmetric antenna pairs is below the threshold.

4. The system according to claim 1, wherein the internal object or the change in the already-detected internal object is detected when the difference between the received microwave signals is equal to or above a threshold, and
wherein no internal object or no change in the already detected internal object is detected when the difference between the received microwave signals at symmetric antenna pairs is below the threshold.

5. The system according to claim 1, wherein the antennas are configured to be symmetrically positioned and asymmetrically oriented, differences between the received microwave signals and a reference measurement changing as a function of time and being indicative of a presence of the internal object.

6. The system according to claim 1, wherein the system is configured to obtain the representation of the at least one received microwave signal at each of the antennas that is a receiver antenna, the representation of the received microwave signal being used when comparing received microwave signals.

7. The system according to claim 1, wherein the internal object is a liquid.

8. The system according to claim 1, wherein the body is the head or the abdomen.

9. A method performed by a system for detecting an internal object in a body, the internal object and the body having different dielectric properties, the body being initially substantially symmetric and having a symmetry line which represents a division of the body in two body parts that are counterparts, each of the body parts on a respective side of the symmetry line being substantially symmetric in shape, each of the body parts on the respective side of the symmetry line being initially substantially symmetric in content when no internal object is located in the body, the internal object being asymmetrically disposed with respect to the symmetry line of the body when the internal object is located in the body, the system including at least one antenna pair including two antennas configured to be positioned directly opposite one another in relation to the body and on opposite sides of the symmetry line in the respective counterparts of the body such that one of the antennas in the antenna pair is configured to be symmetrically positioned around the body with respect to the other antenna in the antenna pair and in relation to the symmetry line, the method comprising: transmitting at least one microwave signal into the body from at least one of the antennas, the transmitted at least one microwave signal being reflected and/or scattered from the internal object;
receiving reflected and/or scattered microwave signal at one or more of: (i) the other antenna and (ii) the transmitting antenna whereby the one or more of the other antenna and the transmitting antenna is operated as a receiver after the transmitting antenna transmits the at least one microwave signal or the one or more of the other antenna and the transmitting antenna is operated as a receiver at the same time as the one or more of the other antenna and the transmitting antenna is transmitting;

comparing the received microwave signals at the symmetrically positioned antennas; and detecting, based on an analysis of one or more of: (i) a plurality of asymmetries, and (ii) changes in asymmetries in the received microwave signals, the internal object or a change in an already-detected internal object when there is a difference between the received microwave signals at symmetric antenna pairs, the asymmetries including asymmetries in received p-n sequence data of the received microwave signals, the difference being related to the different dielectric properties between the internal object and the body, wherein the body is one of a head, a brain, an abdomen, a thorax, and a leg, and wherein the antennas of each of the at least one antenna pair are directly opposite one another with respect to the body on a plane passing through the body and perpendicular to the symmetry line.

10. The method according to claim 9, further comprising: determining a type of the internal object or properties of the internal object based on the difference between the received microwave signals at symmetric antenna pairs related to the different dielectric properties and their spatial distribution.

11. The method according to claim 9, further comprising: obtaining a representation of the at least one received microwave signal at each of the antennas that is a receiver antenna, the representation of the received microwave signal being used when comparing received microwave signals.

12. The method according to claim 11, wherein the representations of the at least one received microwave signal at each receiver antenna are normalized with a common normalization factor before analyzing and comparing the received microwave signals.

13. The method according to claim 9, wherein the difference between the received microwave signals at symmetric antenna pairs during a period of time is analyzed and is used to detect a presence or a change of properties of the internal object.

14. The method according to claim 9, wherein the two antennas in the at least one antenna pair are symmetrically positioned around the body in relation to the line of symmetry in the body so that one of the two antennas is at a first position on one side of the line of symmetry and the other antenna of the two antennas is at a corresponding and symmetric second position on the other side of the line of symmetry, wherein the first and second positions are symmetrical positions on each side of the line of symmetry.

15. The method according to claim 9, wherein the at least one antenna pair comprises two antenna pairs, wherein one of the antennas in one of the antenna pairs is common between the two antenna pairs, the common antenna is configured to be positioned on the symmetry line, remaining antennas of the antennas other than the common antenna are configured to be symmetrically positioned around the body in relation to the line of symmetry in the body so that one of the antennas is at a first position on one side of the line of symmetry and another antenna of the antennas is at a corresponding and symmetric second position on the other side of the line of symmetry, and the first and second positions are symmetrical positions on each side of the line of symmetry.

16. The method according to claim 9, wherein the two antennas in the at least one antenna pair are positioned with the same angle in relation to the line of symmetry.

17. The method according to claim 9, wherein the body is initially a substantially symmetric body and the internal object is asymmetrically located in the substantially symmetric body.

18. The method according to claim 9, wherein the internal object or the change in the already-detected internal object is detected when the difference between the received microwave signals is equal to or above a threshold, and wherein no internal object or no change in the already detected internal object is detected when the difference between the received microwave signals at symmetric antenna pairs is below the threshold.

19. The method according to claim 9, where the antennas are configured to be symmetrically positioned and asymmetrically oriented, differences between the received microwave signals and a reference measurement changing as a function of time and being indicative of a presence of the internal object.

* * * * *